United States Patent
DiMagno et al.

(10) Patent No.: US 7,592,486 B2
(45) Date of Patent: Sep. 22, 2009

(54) ANHYDROUS FLUORIDE SALTS AND REAGENTS AND METHODS FOR THEIR PRODUCTION

(75) Inventors: Stephen G. DiMagno, Lincoln, NE (US); Haoran Sun, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 312 days.

(21) Appl. No.: 11/226,277

(22) Filed: Sep. 15, 2005

(65) Prior Publication Data

US 2006/0089514 A1  Apr. 27, 2006

Related U.S. Application Data

(60) Provisional application No. 60/610,412, filed on Sep. 16, 2004.

(51) Int. Cl.
*C07C 211/63* (2006.01)
(52) U.S. Cl. .......................... 564/281; 568/9
(58) Field of Classification Search ................. 564/281; 568/9
See application file for complete search history.

(56) References Cited

U.S. PATENT DOCUMENTS

| | | | |
|---|---|---|---|
| 5,369,212 | A | 11/1994 | Christe |
| 5,854,084 | A | 12/1998 | Drukier |
| 6,156,812 | A | 12/2000 | Lau |
| 6,451,921 | B2 | 9/2002 | Weisse |
| 6,794,401 | B2 | 9/2004 | Nag |

FOREIGN PATENT DOCUMENTS

CA  2035561  11/1991

OTHER PUBLICATIONS

CheMBioChem Special Issue: Fluorine in the Life Sciences 2004, 5, 557726.
Christe, K.O., et al., J. Am. Chem. Soc. 1990, 112, 7619-25.
Gnann, R.Z., et al., J. Am. Chem. Soc. 1997, 119,112-115.
Kornath, A., et al. Inorg. Chem. 2003, 42, 2894-2901.
JACS, 1990, 112, 7619-7625.
.J.Am.Chem.Soc., Bennett, B.K. et al., 1994, 116, 11165-11166.
JACS, 1997, 119, 112-115.
Inorg. Chem., 2003, 42, 2894-2901.
Cox, D.P., et al., J. Org. Chem. 1984, 49, 3216-19.
Shannn, R.K., et al., J. Org. Chem. 1983, 48, 2112-14.
Pilcher, et al. J. Am. Chem. Soc. 1995, 117, 5166-5167.
Akiyama, Y, et al., S. Synlett 2003, 1530-1532.

*Primary Examiner*—Shailendra Kumar
(74) *Attorney, Agent, or Firm*—Thompson Coburn LLP; Steven M. Ritchey, Esq.

(57) ABSTRACT

Anhydrous organic fluoride salts and reagents prepared by a method comprising the nucleophilic substitution of a fluorinated aromatic or fluorinated unsaturated organic compound with a salt having the formula:

$$[Q_nM]^{x+}A_x^-$$

in an inert polar, aprotic solvent; wherein M is an atom capable of supporting a formal positive charge, the n groups Q are independently varied organic moieties, n is an integer such that the [$Q_nM$] carries at least one formal positive charge, x is an integer defining the number of formal positive charge(s), +, carried by the [$Q_nM$], $A^-$ is an anionic nucleophile capable of substituting for F in the fluorinated compound and F represents fluorine or a radioisotope thereof.

16 Claims, 10 Drawing Sheets

ANHYDROUS FLUORIDE SALTS AND REAGENTS AND METHODS FOR THEIR PRODUCTION

This application claims benefit of 60/610,412, filed Sep. 16, 2004.

FIELD OF THE INVENTION

The invention relates to novel organic fluorides and methods for their production.

BACKGROUND OF THE INVENTION

Fluorine substitution is a powerful tool to improve the bioavailability of pharmaceuticals and agrochemicals. Thus, an expansive set of nucleophilic and electrophilic reagents have been developed to replace various C—X functional groups with C—F.
[CheMBioChem Special Issue: Fluorine In the Life Sciences 2004, 5, 557726]. Simplest among the nucleophilic fluorinating reagents are "anhydrous" or "naked" organic fluoride salts, represented by tetramethylammonium fluoride (TMAF) [Christe, K. O, et al, *J. Am. Chem. Soc.* 1990, 112, 7619-25, 1-methylhexamethylenetetramine fluoride (MHAF) [Gnann, R. Z., et al, *J. Am. Chem. Soc.* 1997, 119, 112-115] and tetramethylphosphonium fluoride (TMPF) [Kornath, A, et al, *Inorg. Chem.* 2003, 42, 2894-2901]. Highly soluble anhydrous fluoride salts possessing a wide variety of alkyl groups are desirable for synthetic purposes, but these compounds cannot be prepared according to current methodologies.

Typical of prior art methods for preparing such salts are those described in U.S. Pat. No. 5,369,212 and Canadian patent no. 2035561.

The preparation of absolutely anhydrous fluoride salts whose cations are substituted with alkyl groups possessing beta-hydrogen atoms has proved to be a significant challenge. Approximately 20 years ago, the first claims for "anhydrous" tetrabutylammonium fluoride appeared. The compounds were prepared by physical drying of the hydrated salt, i.e., dynamic high vacuum (<0.1 mmHg) to remove water for at least 48 hours from TBAF·3H$_2$O at 40–45° C. (JOC, 1984, 49, 3216-3219). However, there was still 0.1 to 0.3 equiv of water in this "anhydrous" TBAF and copius quantities of the elimination products (tributylamine, bifluoride ion, and butane) as a result of this process. The side reactions and the presence of water and tributylamine significantly decrease the reactivity of the fluoride ion and lead to significant side reactions, such as hydrolysis of the starting substrates. An example of water's deleterious effects upon the reactivity of TBAF can be seen in simple model reactions. For example, if TBAF that is dried using physical methods is combined with benzyl chloride or benzyl bromide at room temperature to 40° C., formation of benzyl fluoride required 8 to 12 hours. In comparison, if truly anhydrous TBAF were employed, the same reaction would only take a few minutes or less at low temperatures and give quantitative yields.

Later, individual syntheses of tetramethylammonium fluoride (TMAF) (JACS, 1990, 112, 7619-7625), cobaltocenium fluoride (Cp$_2$CoF), (JACS, 1994, 116, 11165-11166), 1-Methylhexamethylenetetramine fluoride (MHAF) (JACS, 1997, 119, 112-115), tetramethylphosphonium fluoride (TMPF) (Inorg. Chem., 2003, 42, 2894-2901) as well as several others were synthesized and characterized as "naked" or "anhydrous" fluoride salts. However, each of these salts has specific drawbacks in terms of solubility or reactivity, and the preparative methods for synthesizing these individual salts are not applicable for the preparation of a wide variety of fluoride salts. Anhydrous fluoride salts with alkyl groups capable of beta-elimination (ethyl, propyl, butyl, isopropyl, pentyl, isobutyl, etc.) in particular are not accessible by current methods.

Generally, then, these compounds are commonly prepared in a hydrated state and are subsequently dried by heating under dynamic vacuum or by azeotropic distillation. However, the conditions used to dry these salts are often incompatible with a variety of desirable cations. For example, dried tetrabutylammonium fluoride, (TBAF) [Cox, D. P., et al, *J. Org. Chem.* 1984, 49, 3216-19] is reported to decompose by Hofmann elimination at room temperature. The salt isolated after dehydration is contaminated with copious amounts of bifluoride ion (HF$_2$) and tributylamine [Shannn, R. K., et al, *J. Org. Chem.* 1983, 48, 2112-14]. These considerations and findings have led to the belief among those skilled in the art that "it is very unlikely that pure, anhydrous tetraalkylammonium fluoride salts have ever, in fact, been produced in the case of ammonium ions susceptible to E2 eliminations" [Sharma et al, supra].

It is an object of the present invention to provide a novel method of producing truly anhydrous organic fluoride salts and reagents.

It is a further object of the invention to provide novel anhydrous organic fluoride salts and reagents.

SUMMARY OF THE INVENTION

The above and other objects are realized by the present invention one embodiment of which relates to a method of synthesizing an anhydrous fluoride salt having the formula:

comprising the nucleophilic substitution of a fluorinated aromatic or fluorinated unsaturated organic compound with a salt having the formula:

in an inert polar, aprotic solvent; wherein M is an atom capable of supporting a formal positive charge, the n groups Q are independently varied organic moieties, n is an integer such that the [Q$_n$M] carries at least one formal positive charge, x is an integer defining the number of formal positive charge(s), +, carried by the [Q$_n$M], A$^-$ is an anionic nucleophile capable of substituting for F in the fluorinated compound and F represents fluorine or a radioisotope thereof.

Another embodiment of the invention concerns anhydrous organic fluoride salts and reagents of the above formula, preferably produced by the above-described invention.

Still other embodiments of the invention relate to the use of the anhydrous organic fluoride salts and reagents of the invention in methods, processes and syntheses wherein the non-anhydrous salts and reagents are employed.

DETAILED DESCRIPTION OF THE INVENTION

The present invention is predicated on the discovery that a wide variety of truly anhydrous organic fluoride salts and reagents may be synthesized in one step by the nucleophilic substitution of various fluorinated organic compounds with organic salts of diffusely charged anionic nucleophiles capable of forming strong bonds to carbon in a nucleophilic substitution reaction. Thus, employing the methods of the invention a wide range of novel anhydrous salts can be prepared using one simple procedure. Moreover, as the examples set forth below demonstrate, the method of the invention allows many sensitive or unstable fluoride salts to be prepared easily. Such compounds would decompose rapidly under the conditions employed in typical literature preparations of similar compounds.

Although the invention is principally exemplified and illustrated herein for preparing tetrabutylammonium fluoride, it will be understood by those skilled in the art that the inventive method may be utilized to prepare many and varied anhydrous fluoride salts. It will also be understood by those skilled in the art that the method of the invention may also be utilized to prepare radioisotopic fluoride salts (e.g., $^{18}$F).

The reaction may be carried out at low temperatures [−35° C. to RT] in polar aprotic solvents such as tetrahydrofuran, dimethyl sulfoxide, diethyl ether, dioxane, dimethoxyethane, methyl tert-butyl ether, acetonitrile, acetone, methylethylketone, tetrahydrofuran, dimethylformamide, dimethylacetamide, N-methylpyrolidinone, butyronitrile, or in aromatic solvents such as toluene, pyridine, benzonitrile, or diphenyl ether. Other suitable solvents include carbonates such as diethyl carbonate and hexamethylphosphoric triamide. In preferred embodiments tetrahydrofuran, dimethylsulfoxide, and acetonitrile are the solvents employed. Halogenated solvents such as methylene chloride or dichloroethane are decomposed rapidly by anhydrous fluoride salts, and are thus generally not useful for this synthetic procedure.

In the above-described formulae, Q is an organic moiety capable of undergoing E2 elimination and may be, e.g., alkyl, alkenyl, alkynyl, or form the backbone or sidechain of a polymer. M may be N, P or any element capable of supporting a formal positive charge. The anion A may any diffusely charged anionic nucleophile capable of forming strong bonds to carbon in a nucleophilic substitution reaction, such as, e.g., cyanide, isothiocyanate, thiocyanate, alkyl- and arylthiolates, or azide. In preferred embodiments cyanide is the nucleophile employed.

$[Q_nM]^{x+}A_x^-$ is preferably a tetraalkylammonium cyanide, a trialkylarylammonium cyanide, a dialkyldiarylammonium cyanide, an alkyltriarylammonium cyanide, or a tetraarylammonium cyanide; Q being an organic moiety capable of undergoing E2 elimination.

The fluorinated compound nucleophically substituted in the method of the invention is preferably a fluorinated benzene, alkene or alkyne with a large number of fluorine atoms per unit weight e.g., hexafluorobenzene, octafluoronaphthalene, octafluorotoluene, pentafluorobenzonitrile, pentafluoropyridine, decafluorobiphenyl, etc. For the generation of isotopically labeled anhydrous fluoride salts (i.e., TBA $^{18}$F) a singly fluorinated arene is sufficient, e.g., 4-fluorobenzonitrile.

The reaction scheme for the method of the invention is:

Nucleophile substitution reactions are generally well known in the art as exemplified in U.S. Pat. Nos. 6,794,401; 6,451,921; 6,156,812 and 5,854,084, inter alia.

Thus tetrabutylammonium fluoride (TBAF) is easily prepared in one step at low temperatures by the nucleophilic substitution of the hexafluorobenzene with tetrabutylammonium cyanide. Adventitious water is readily scavenged by the hexacyanobenzene by-product of the reaction.

The constraints on a fluoride-generating synthesis grounded in nucleophile substitution reactions are quite severe and dictate a careful choice of the nucleophile. Because the enthalpic driving force for fluoride liberating reaction derives almost exclusively from ion-pairing and ΔBDE terms, and because the $C_{sp2}$—F bond in aromatics (as well as unsaturated compounds) is exceptionally strong (126 kcal/mol), only diffusely charged anionic nucleophiles capable of forming strong bonds to carbon are capable of acting in nucleophile substitution reactions reactions at low temperature in polar aprotic solvents. Cyanide ion, a potent, weakly basic nucleophile that forms strong bonds to sp2-hybridized carbon (BDE=133 kcal/mol) is an excellent candidate. It will be understood by those skilled in the art, however, that any similar diffusely charged anionic nucleophile may also be employed in the method of the invention, such as, e.g., isothiocyanate, isocyanate, cyanate, thiocyanate, alkyl- and arylthiolates, or azide.

As illustrated in the examples below, treatment of hexafluorobenzene with tetrabutylammonium cyanide (TBACN) (in 1:1 to 1:6 molar ratios) in the polar aprotic solvents THF, acetonitrile, or DMSO at or below room temperature gives excellent yields of anhydrous TBAF. $^{19}$F NMR spectroscopy indicates that the overall yield of TBAF in solution in all cases is >95%. Cyano substitution dramatically increases the fluorinated benzene ring's susceptibility to further nucleophilic attack, as is evidenced by the observation of pentacyanofluorobenzene and hexafluorobenzene as the principal fluorinated aromatic species in the reaction solution, even if 1:1 TBACN:$C_6F_6$ stoichiometry is employed.

In THF, colorless to light yellow anhydrous TBAF precipitated from cooled (−35° C.) solutions and yields of the isolated salt ranged from 40% to 70%. Freshly isolated TBAF displayed one singlet $^{19}$F NMR signal at −86 ppm in THF and four $^1$H NMR signals for the TBA cation. The characteristic doublet of $HF_2^-$ at δ=−147 ppm ($J_{H-F}$=128 Hz) was observed in freshly prepared solution samples, and in samples precipitated from THF and redissolved. The concentration of TBA $HF_2^-$ was generally less than 2% that of TBAF. Solid anhydrous TBAF is stable under nitrogen at −35° C. for weeks. TBAF decomposes slowly in THF or in the solid state by E2 elimination if warmed above 0° C.

TBAF can be prepared conveniently in situ in polar aprotic solvents at room temperature and used without isolation or purification. Treatment of $(CD)_3SO$ or $CD_3CN$ solutions of TBACN with $C_6F_6$ (at 25° C.) gave highly colored, concentrated (up to 2 M) solutions of TBAF exhibiting the characteristic $^{19}$F NMR signals for ion-paired fluoride (Table 1). Small amounts (generally <4%) of $HF_2^-$ are also generated in these solvents. TBAF is stable for hours in $CD_3CN$ and for more than 24 h in DMSO at 25° C.

TABLE 1

$^{19}$F NMR data of anhydrous fluoride salts

| Compd | Solvent | Chemical Shift |
|---|---|---|
| TBAF | THF | −86 ppm |
|  | $CD_3CN$ | −72 ppm |
|  | $(CD_3)_2SO$ | −75 ppm |
| TMAF | $(CD_3)_2SO$ | −75 ppm$^a$ |
|  | $CD_3CN$ | −74 ppm |
| TMPF | $CD_3CN$ | −70 ppm |

$^a$generated in situ with TMACN.

The origins of the unexpected stability of TBAF in THF, $CH_3CN$, and DMSO lie in the relatively low temperatures used for generation of the salt, and in the dehydrating properties of the main reaction byproduct, hexacyanobenzene. Hexacyanobenzene has been shown to add water to form the strong acid pentacyanophenol (pKa=2.9). Thus, adventitious water is removed from solution during the course of the initial fluoride-generating nucleophilic reaction, forming two equivalents of bifluoride ion per equivalent of water and the innocuous byproduct TBA pentacyanophenoxide. Added water (0.08 eq.) is scavenged from TBAF solutions prepared in this manner, as is evidenced by time-dependent changes in the linewidth and chemical shift of the fluoride ion $^{19}$F NMR resonance, and by the generation of 0.16 eq. of $HF_2^-$.

It has been shown that the addition of alkoxide nucleophiles to hexacyanobenzene is rapid under basic conditions, and that the resultant pentacyanophenyl alkyl ethers are subject to $S_N2$ displacement. This pathway is amply demonstrated by the direct fluorination of simple alcohols. For example, if excess TBAF (12 eq.) is generated in situ in $(CD_3)_2SO$ and used directly, benzyl alcohol is converted quantitatively to benzyl fluoride, presumably via the intermediacy of benzyl pentacyanophenyl ether. Thus, generation of TBAF in the presence of hexacyanobenzene can provide DAST-like deoxofluorination of alcohols.

Given that fluoride, the smallest anion (ionic radius=1.33 Å) forms extremely strong bonds to protons (H—F BDE=136 kcal/mol, $HF_2^-$ BDE=46 kcal/mol) $F^-$ is expected to be an aggressive Brønsted base. It has been shown that TMAF deprotonates $CD_3CN$ over the course of several hours consuming $F^-$ to form $DF_2^{-2}$. A similar process is observed with TBAF in $CD_3CN$; nevertheless, no decomposition of the TBA cation is observed over the course of 24 hours. In contrast, no deuterium exchange is observed in solutions of TBAF in $(CD_3)_2SO$ over the same time period. These results do not, however, allow a good estimate of the ion-pair basicity of fluoride ion in polar aprotic solvents, since slow rates of proton transfer and side reactions may preclude generation of a true equilibrium mixture. An additional complication is that any proton transfer to fluoride ion is followed by a rapid conversion to $HF_2^-$ under these conditions.

The kinetic barriers inherent in the proton transfer from C—H bonds to $F^-$ are apparent in the following example. While $(CD_3)_2SO$ does not undergo proton exchange with residual $HF_2$ in TBAF solutions, if a $(CD_3)_2SO$ solution of purified TBAF (precipitated from THF) is spiked with water (0.08 eq.), a slow (2 h) conversion of $HF_2^-$ to $DF_2^-$ is observed. Deuterium exchange occurs without a detectable increase in the bifluoride ion concentration, indicating that deprotonation of water by TBAF is strongly disfavored under these conditions (see FIG. 1). Upon standing, hydrated DMSO solutions of purified TBAF evolve butene and tributylamine by E2 elimination, demonstrating the sensitivity of TBAF to hydroxylic impurities in polar aprotic solvents.

The anhydrous organic fluoride salts of the invention find utility in a wide variety of methods, processes, reactions and syntheses employing the corresponding non-anhydrous fluoride salts. The substitution of the anhydrous fluoride salts of the invention in these methods gives rise to more efficient reactions leading to higher yields of the desired product and the production of undesired reaction conditions and by-products. Exemplary of such reactions are a) nucleophilic substitution reactions of alkyl halides, tosylates, and triflates; b) nucleophilic substitution reactions of nitroaromatics, chloroaromatics, and aromatic triflates, and c) for the deprotection of silylated species. Again, however, it will be understood by those skilled in the art that the anhydrous salts of the invention may be utilized to good effect in any reaction or method where the use of the corresponding non-anhydrous salt is applicable. It will also be understood by those skilled in the art that the anhydrous salts of the invention may be employed in the form of the reaction mixture produced by the method of the invention or may be separated therefrom before use according to any conventional method for separating organic salts from their reaction products, such as, e.g., use of ion exchange resins, chiral chemistry and the like.

Reactions employing TBAF generated in situ in accordance with the method of the invention are summarized in Table 2. For nucleophilic fluorination, anhydrous TBAF is comparable to, or exceeds the reactivity of other nucleophilic fluorinating agents. In head-to-head comparisons, TBAF exhibits dramatically enhanced rates of fluorination compared to dynamic vacuum dried "anhydrous" TBAF, $CoCp_2F$, or TBAT. Neither heating nor a gross excess of TBAF is generally required to effect substitution (Table 2).

TABLE 2

Fluorination of various substrates using anhydrous TBAF

| Run | Substrate | Reagent | Solvent | Conditions | Product | Yield* (%) | Comments | Ref. |
|---|---|---|---|---|---|---|---|---|
| 1 | $PhCH_2Br$ | 1.3~1.5 eq. TBAF | $CD_3CN$ | −35° C., <5 min | $PhCH_3F$ | 100 | | This work |
| 2 | $PhCH_2Br$ | 2 eq. TBAF "anhydrous" | THF | RT, 8 h | $PhCH_3F$ | >90 | $PhCH_2OH$ (5%) | 3 |
| 3 | $CH_3I$ | 1.5 eq. TBAF | $CD_3CN$ | −40° C., <5 min | $CH_3F$ | 100 | | This work |
| 4 | $CH_3I$ | $CoCp_2F$ | THF | RT, 6 h | $CH_3F$ | 100 | | This work |
| 5 | $CH_3(CH_2)_2Br$ | TBAF | THF | RT, <5 min | $CH_3(CH_2)_3F$ | 40-50 | (remainder alkene) | This work |
| 6 | $CH_3(CH_2)_2Br$ | 6 eq. TBAT | $CD_3CN$ | Reflux, 24 h | $CH_3(CH_2)_3F$ | 85 | | This work |
| 7 | $CH_3(CH_2)_2Br$ | 2 eq. TBAF "anhydrous" | THF | RT, 1 h | $CH_3(CH_2)_3F$ | 48 | 40% octanol | 3 |
| 8 | $ClCH_2CH_2$—O—SO$_2$—C$_6$H$_4$—Cl | TBAF | THF | RT, <5 min | $CH_3(CH_2)_{13}F$ | 100 | | This work |
| 9 | TsO-/-OTs (dioxolane) | 4 eq. TBAF | THF, or $CD_3CN$ | RT, <5 min | F-/-F (dioxolane) | >90 | | This work |
| 10 | 3,5-bis(CF$_3$)-nitrobenzene | 1.3 eq. TBAF | $CD_3CN$ | RT, <2 min | 3,5-bis(CF$_3$)-fluorobenzene | >95 | | This work |
| 11 | PhCOCl | 1 eq. TBAF | THF | RT, <2 min | PhCOF | 100 | | This work |
| 12 | Tosyl-Cl | 1 eq. TBAF | THF | RT, <2 min | Tosyl-F | 100 | | This work |

*yields were calculated by integration of starting material and product signals in the $^1H$ and/or $^{13}F$ NMR spectra.

Taken together, the results presented here show that exceptionally nucleophilic, highly soluble fluoride ion sources featuring ammonium cations can be prepared readily even if the cations are thought susceptible to E2 elimination. The self dehydrating nature of the nucleophilic aromatic substitution method makes it an exceptionally forgiving synthetic route to anhydrous fluoride salts.

Generally, the method of the invention produces anhydrous organic fluoride salts and reagents containing less than 0.01% $H_2O$ in one efficient step, in high yields and low temperatures without deleterious effects on the product or reaction mechanism. Moreover, the reactivity of the anhydrous fluoride salts of the invention in solution or liquid approaches that of conventional fluoride salts in the gas phase, e.g., a reaction between nitrobenzene and conventionally produced organic fluoride salt in solution will not proceed but will in gas phase. The anhydrous fluoride salts of the invention will react with nitrobenzene in solution.

EXAMPLES

All reagents were handled under $N_2$. Hexafluorobenzene ($C_6F_6$) (99%, SynQuest) was passed through a column of activated (130° C. for 5 h) silica gel and distilled from $CaH_2$. Acetonitrile (HPLC grade, Aldrich) was distilled from $P_2O_5$ and redistilled under reduced pressure from $CaH_2$. THF (anhydrous, Aldrich) was distilled from $LiAlH_4$. Purified solvents were stored under $N_2$ in Schlenk-style flasks under $N_2$. Tetra-n-butylammonium cyanide (TBACN) (97%) was obtained from Fluka Chemical Co. TBACN was dried under vacuum at 40° C. overnight prior to use. For initial work, TBACN was recrystallized from THF/Hexane by layering, subsequent studies showed that this purification step was unnecessary. Tetramethylammonium hexafluorophosphate ($TMAPF_6$) was obtained from Fluka and dried under vacuum. All other reagents were of analytical grade, from Aldrich. All chemical handling was performed under $N_2$ in a glove box.

$^1H$, $^{13}C$ and $^{19}F$ NMR spectra were determined in the Instrumentation Center at the University of Nebraska-Lincoln. 400 MHz (QNP probe for $^1H$, $^{13}C$ and $^{19}F$ NMR spectra), 500 MHz (QNP probe for $^1H$, $^{13}C$ and $^{19}F$ NMR spectra) and 600 MHz (HF probe for $^1H$ and $^{19}F$ NMR spectra) NMR spectrometers were used in this study. $^{19}F$ NMR chemical shifts were referenced to an internal standard, hexafluorobenzene

Syntheses of TBAF

Anhydrous tetrabutylammonium fluoride (TBAF):

0.67 g TBACN was dissolved in 2.5 ml THF and the resulting solution was cooled to −65° C. A chilled solution (−65° C.) of 0.3 ml hexafluorobenzene ($C_6F_6$) in 0.5 ml THF was added, and the mixture was allowed to warm gradually (over 4 hours) to −15° C. During this time the solution changed from colorless to yellow-green, and a white solid precipitated. The mixture was again cooled to −65° C., the solid was filtered and washed two times with cold THF. All isolation procedures were kept below −36° C. The white or light yellow TBAF solid was collected and put into a −36° C. freezer for short term storage. Total TBAF yield was over 95% (based upon TBACN, confirmed by quenching experiments with benzyl chloride) if the mixture was used directly. Isolated yields of the solid material varied from 40% to 70% depending on the rapidity of the wash and filtration steps. $^1$H NMR (($CD_3$)$_2$SO) 3.23 (8H, m), 1.56 (8H, m), 1.28 (8H, sext, J=7.31 Hz), 0.86 (12H, t, J=7.31 Hz); $^{19}$F NMR (($CD_3$)$_2$SO) −72.6 ppm (s); $^{13}$C NMR (($CD_3$)$_2$SO): 57.5, 23.1, 19.2, 13.5 ppm.

Figure 1:
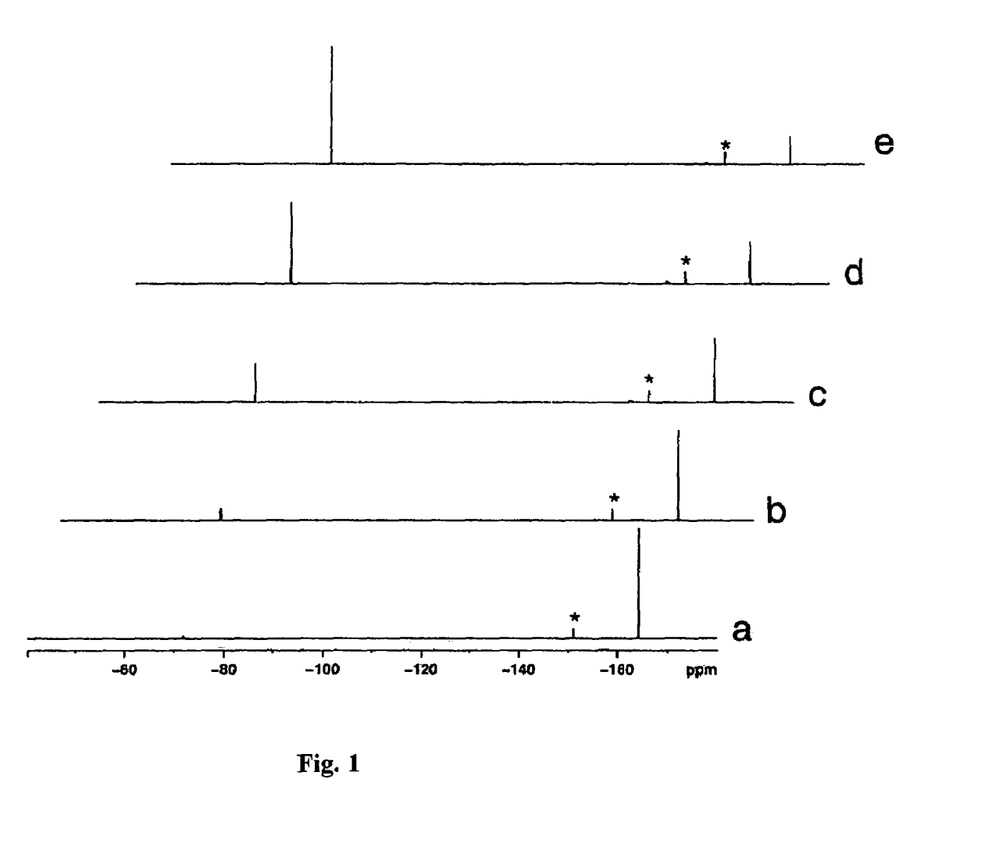
FIGS. 1-10 depict $^{19}$F NMR and $^1$H NMR spectra for various reaction products produced by the reactions described herein (vide infra).

Generation of TBAF in $CH_3CN$:

TBACN (0.134 g, 0.5 mmol) was dissolved in anhydrous acetonitrile (0.5 ml). At 25° C., 9.6 μl (0.083 mmol) $C_6F_6$ was added, and the initially colorless solution changed to dark-red immediately. The reaction was monitored by $^{19}$F NMR spectroscopy. Fluoride generation was complete within 1 h. A representative $^{19}$F NMR spectrum is shown in FIG. 1.

Generation of TBAF in DMSO:

A very similar procedure was used to generate TBAF in DMSO. TBACN (0.134 g, 0.5 mmol) was dissolved in anhydrous acetonitrile (0.5 ml). At 25° C., 9.6 μl (0.083 mmol) $C_6F_6$ was added, and the mixture was allowed to stand for one h. The solubility of TBAF in both $CH_3CN$ and DMSO was excellent (up to 2 M). The solution was directly used in the fluorination reaction.

TMACN—TMACN was prepared by metathetical ion-exchange of TBACN with $TMAPF_6$ in acetonitrile/THF. 110 mg (0.5 mmol) $TMAPF_6$ was dissolved in a minimum amount of acetonitrile, and a saturated acetonitrile solution of TBACN (134 mg, 0.5 mmol) was added. The precipitated TMACN was filtered, washed with a small amount of acetonitrile, and the residual solvents were evaporated. $^1$H NMR ($CD_3CN$) 3.11 ppm (s), $^{13}$C NMR ($CD_3CN$) 54.27, 167.20.

TMAF—TMAF was synthesized from TMACN and $C_6F_6$ in acetonitrile by a method similar to that described for TBAF. 4.6 mg TMACN dissolve in 0.6 ml of ($CD_3$)$_2$SO at room temperature. 1.0 μl hexafluorobenzene ($C_6F_6$) was and the mixture was allowed to stand at room temperature for 12 h.

General Procedure for Fluorination Reactions

The general procedure given below was used for all fluorination reactions employing in situ generated TBAF. Yields were calculated by integration of the relevant peaks in the $^1$H and $^{19}$F NMR spectra.

In an NMR tube equipped with a PTFE resealable closure, TBACN (0.134 g, 0.5 mmol) was dissolved in anhydrous $CD_3CN$ (or ($CD_3$)$_2$SO) (0.5 ml). At 25° C., 9.6 μl (0.083 mmol) $C_6F_6$ was added, and the mixture was held at room temperature for 1 h. The mixture was cooled to −40° C. and the substrate (0.25-0.5 mmol) was added. The solution was mixed vigorously and the tube was transferred to a precooled (−35° C.) NMR probe and spectra were gathered. The time elapsed from the sample mixing until completion of the first NMR spectrum was approximately 3 min. The reaction was monitored by $^{19}$F NMR spectra every 2 minutes until no further change was observed.

Table 3 shows results of fluorination of various substrates under different conditions. For comparison, the literature results by other fluorination regents are listed in table 3.

TABLE 3

| Run | Substrate | Reagent | Solvent | Temp and Time | Product | Yield (%) | Comments | Ref. |
|---|---|---|---|---|---|---|---|---|
| 1 | $PhCH_2Br$ | 1.3~1.5 eq. TBAF | acetonitrile | −35° C., <5 min | $PhCH_2F$ | 100 | No $PhCH_2OH$ | This work |
| 2 | $PhCH_2Br$ | | DMSO | RT, <2 min | $PhCH_2F$ | 100 | | This work |
| 3 | $PhCH_2Br$ | | THF | RT, <2 min | $PhCH_2F$ | 100 | | This work |
| 4 | $PhCH_2Br$ | 2 eq. TBAF "anhydrous" | THF | RT, 8 hours | $PhCH_2F$ | >90 | $PhCH_2OH$ (5%) | 1 |
| 5 | $PhCH_2Cl$ | 1.5 eq. TBAF | THF | RT, <2 min | $PhCH_2F$ | 100 | | This work |
| 6 | $PhCH_2Cl$ | 2 eq. TBAF "anhydrous" | THF | 40° C., 12 hours | $PhCH_2F$ | | | 1 |
| 7 | $PhCH_2Cl$ | $CoCp_2F$ | THF | RT, 90 min | $PhCH_2F$ | 95 | | 2 |
| 8 | $CH_3I$ | 1.5 eq. TBAF | acetonitrile | −40° C., <5 min | $CH_3F$ | 100 | | This work |
| 9 | $CH_3I$ | $CoCp_2F$ | THF | RT, 6 hours | $CH_3F$ | 100 | | 2 |
| 10 | $CH_3(CH_2)_7Br$ | TBAF | THF | RT, <5 min | $CH_3(CH_2)_7F$ | 40~50 | No octanol | This work |
| 11 | $CH_3(CH_2)_7Br$ | 6 eq. TBAT | acetonitrile | Reflux, 24 h | $CH_3(CH_2)_7F$ | 85 | | 3 |
| 12 | $CH_3(CH_2)_7Br$ | 2 eq. TBAF "anhydrous" | THF | RT, 1 hour | $CH_3(CH_2)_7F$ | 48 | 40% octanol | 1 |
| 13 | $CH_3(CH_2)_{17}$(p-Cl-benzenesulfonate) | TBAF | THF | RT, <5 min | $CH_3(CH_2)_{17}F$ | 100 | | This work |
| 14 | $CH_3(CH_2)_7OTs$ | 2 eq. TBAF "anhydrous" | none | RT, 1 hour | $CH_3(CH_2)_7F$ | 98 | 2% alkene | 1 |

TABLE 3-continued

| Run | Substrate | Reagent | Solvent | Temp and Time | Product | Yield (%) | Comments | Ref. |
|---|---|---|---|---|---|---|---|---|
| 15 | $CH_3(CH_2)_7OTs$ | 4 eq. TBAT | acetonitrile | Reflux, 24 h | $CH_3(CH_2)_7F$ | 99 | Trace alkene | 3 |
| 16 |  | 2 eq. TBAF | THF, or acetonitrile | RT, <5 min |  | 100 | | This work |
| 17 |  | 1.3 eq TBAF | DMSO, or acetonitrile | RT, <8 hours |  | >90 | | This work |
| 18 |  | 1.3 eq TBAF | acetonitrile | RT, <2 min |  | ~95 | | This work |
| 19 | PhCOCl | 1 eq. TBAF | THF | RT or below RT, <2 min | PhCOF | 100 | | This work |
| 20 | PhCOCl | 2 eq. TBAF "anhydrous" | | RT. 1 hour | PhCOF | 81* | | 1 |
| 21 | Tosyl-Cl | 1 eq. TBAF | THF | RT, <2 min | Tosyl-F | 100 | | This work |
| 22 |  | 2.5 eq. TBAF, 3 h; followed by add $H_2O$ | DMSO or acetonitrile | RT, ~3 hours |  | | | This work |
| 23 |  | TBABF-$KHF_2$ | none | 120° C., 2 hours |  | 86 | Contains 10% $PhCHFCH_2OH$ | 4 |

[1]Cox, D. P.; Terpinski, J.; Lawrynowicz, W. J. Org. Chem. 1984, 49, 3216-3219.
[2]Bennett, B. K.; Harrison, R. G.; Richmond, T. G. J. Am. Chem. Soc. 1994, 116, 11165-11166.
[3]Pilcher, A. S.; Ammon, H. L.; DeShong, P. J. Am. Chem. Soc. 1995, 117, 5166-5167.
[4]Akiyama, Y.; Fukuhara, T.; Hara, S. Synlett 2003, 1530-1532.

NMR Spectra:

Generation of TBAF—FIG. 1: $^{19}$F NMR spectra recorded over the course of 40 minutes following the mixing of 134 mg TBACN and 9.6 μl $C_6F_6$ in $CD_3CN$. The peak at =−72 ppm is due to fluoride ion; the peak at □=−164 ppm peak is the $C_6F_6$; the small peak at =−147 ppm (d, $J_{HF}$=148 Hz) is due to $HF_2^-$ (The signal marked with * at −151 ppm is an artifact).

Figure 2:
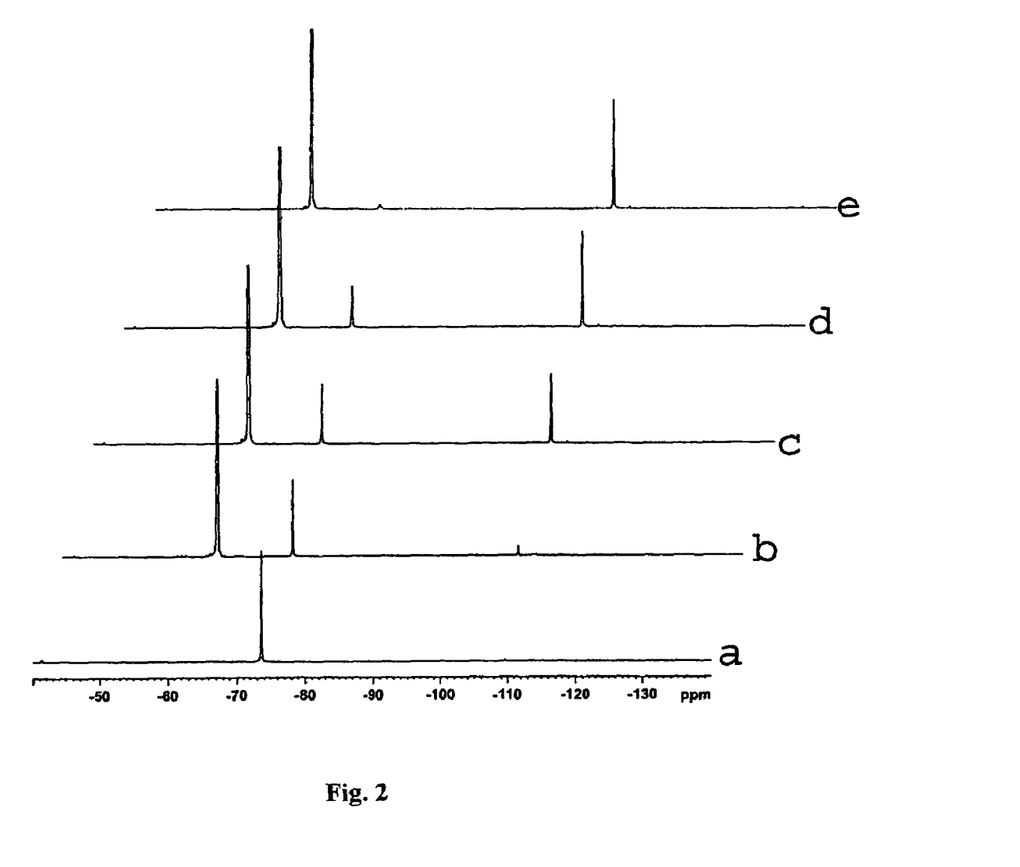

Debromofluorination of an aromatic compound—FIG. 2: Conversion of 3,5-bis(trifluoromethyl)bromobenzene to 3,5-bis(trifluoromethyl)fluorobenzene by TBAF in $(CD_3)_2SO$. a: $^{19}$F NMR spectrum before the addition of 3,5-bis(trifluoromethyl)bromobenzene; b-e: $^{19}$F NMR spectrum after the addition of 3,5-bis(trifluoromethyl)bromobenzene. The total elapsed time was 8 h. Chemical shift assignments: =−74 ppm ($F^-$), =−64 ppm ($CF_3$), =−108 ppm (Ar—F).

Figure 3:
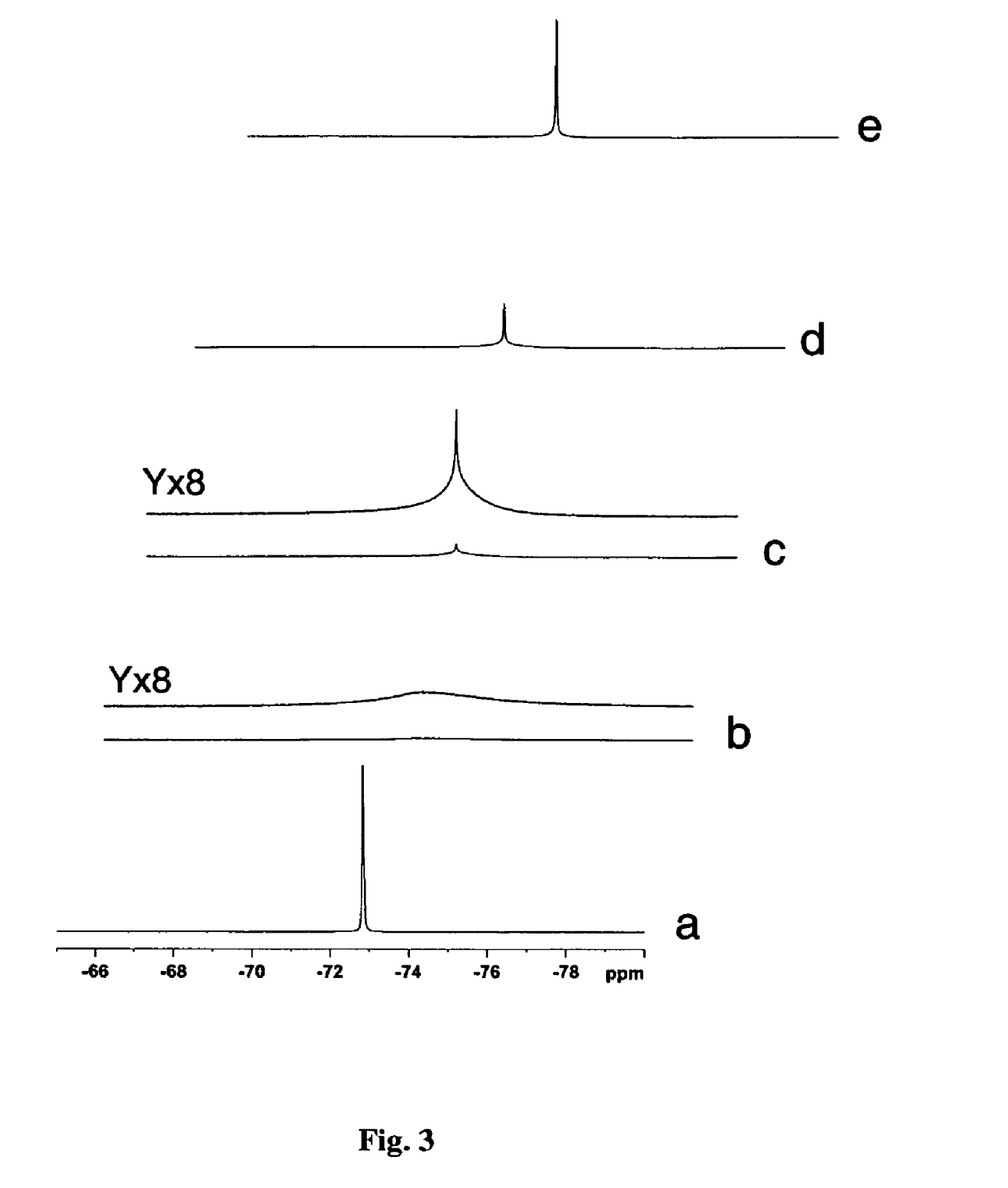

Removal of protic solvent by hexacyanobenzene—FIG. 3: $^{19}$F NMR spectra showing the effect of adding 0.08 eq. benzyl alcohol to a solution of in-situ generated TBAF $(CD_3)_2SO$. a: Spectrum recorded before the addition of benzyl alcohol; b: 5 min after addition of benzyl alcohol; c: 1 h after addition; d: 4 h after addition; e: 20 h after addition. For spectra b and c the bottom spectrum is presented with the normal Y-scale, the top spectrum has the Y-scale multiplied by 8.

Figure 4:
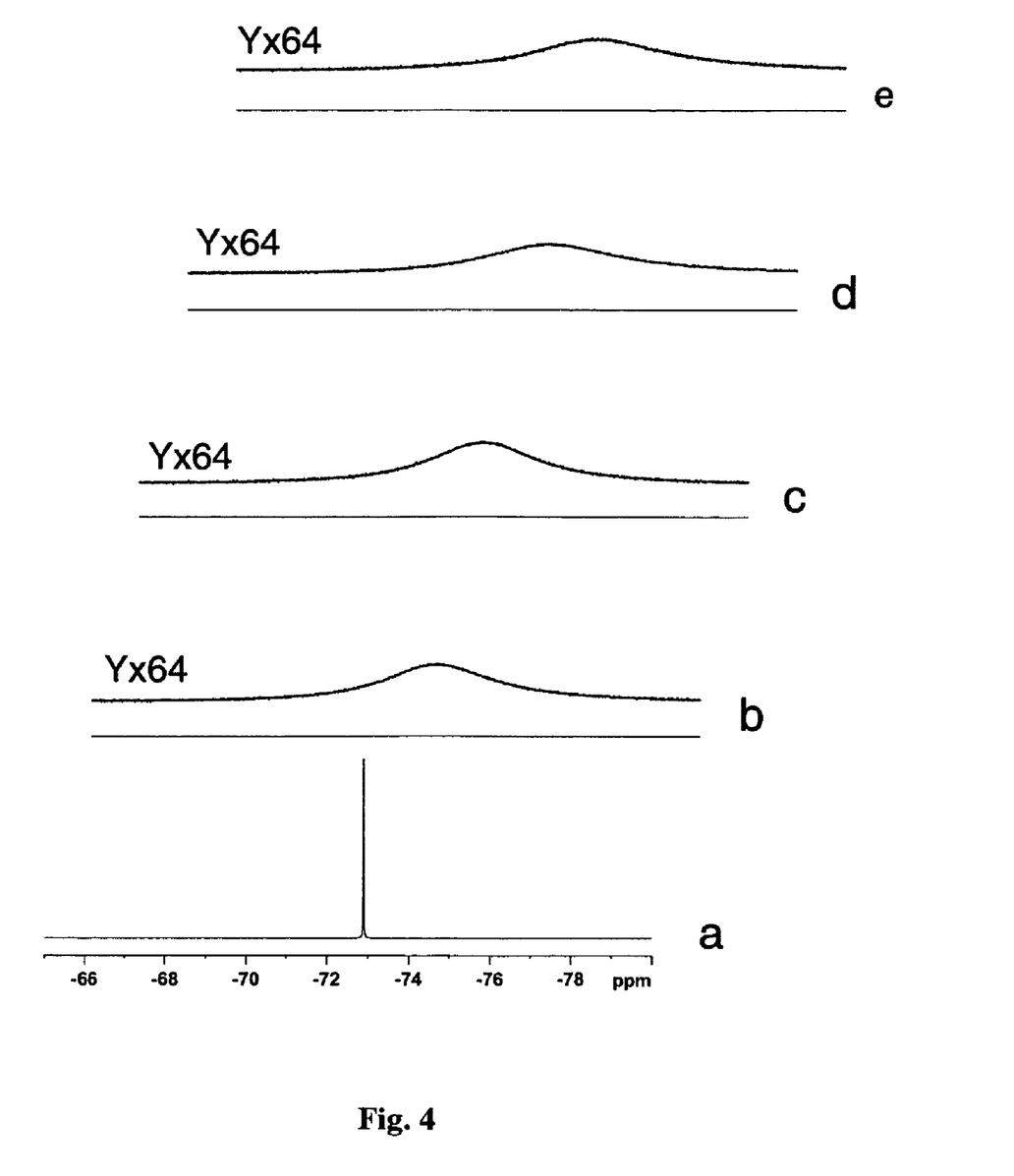

Impact of protic solvent in the absence of hexacyanobenzene—FIG. 4: $^{19}$F NMR spectra showing the effect of adding 0.08 eq. benzyl alcohol to a solution of purified TBAF $(CD_3)_2SO$. a: Spectrum recorded before the addition of benzyl alcohol; b: 10 min after addition of benzyl alcohol; c: 1 h after addition; d: 7 h after addition; e: 20 h after addition. For spectra b and c the bottom spectrum is presented with the normal Y-scale, the top spectrum has the Y-scale multiplied by 64.

Figure 5:
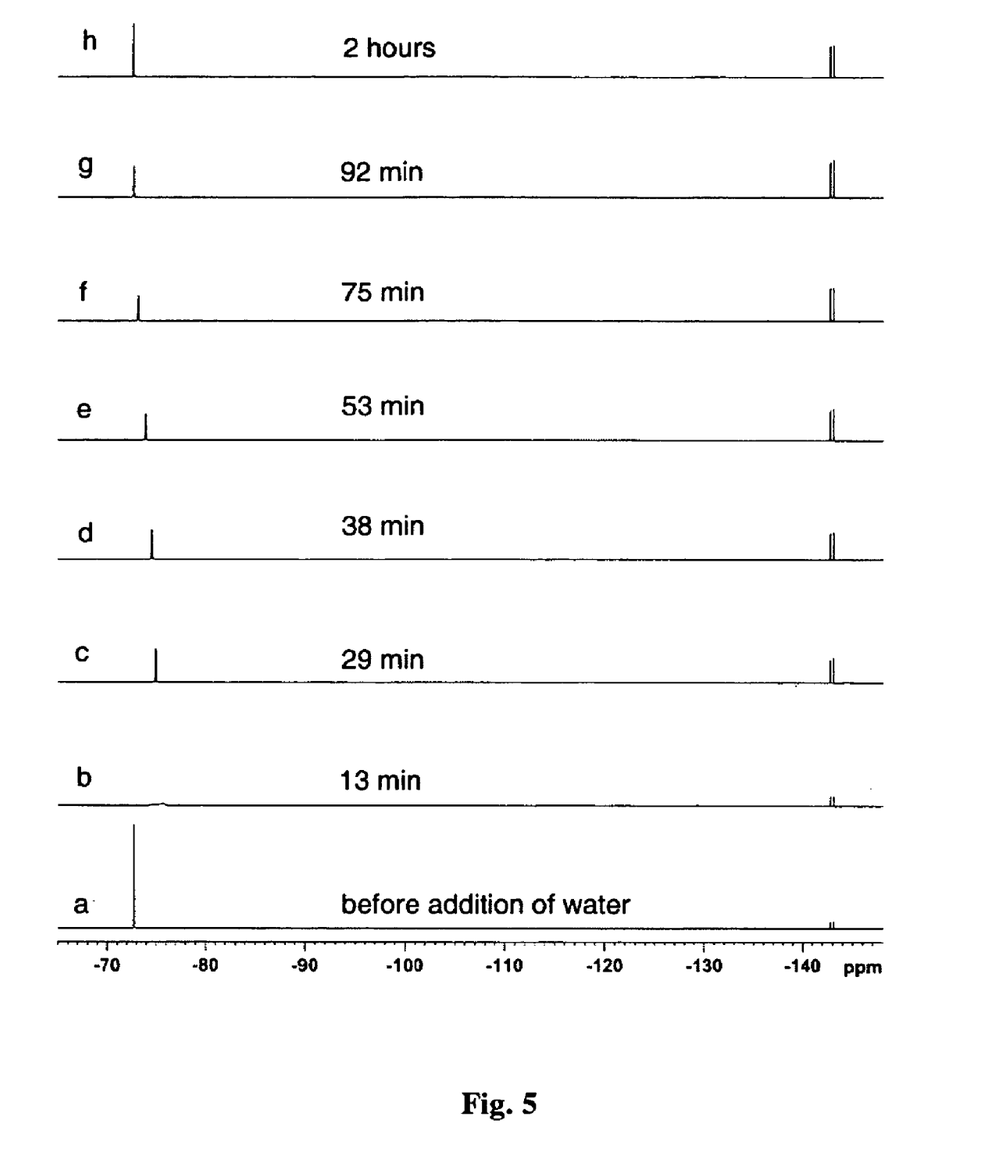

Reaction of in-situ generated TBAF with water—FIG. 5: $^{19}$F NMR spectra of the reaction of in situ generated TBAF with 0.083 eq. water in $(CD_3)_2SO$. a, before addition of water; b~h, after addition of water.

Figure 6:
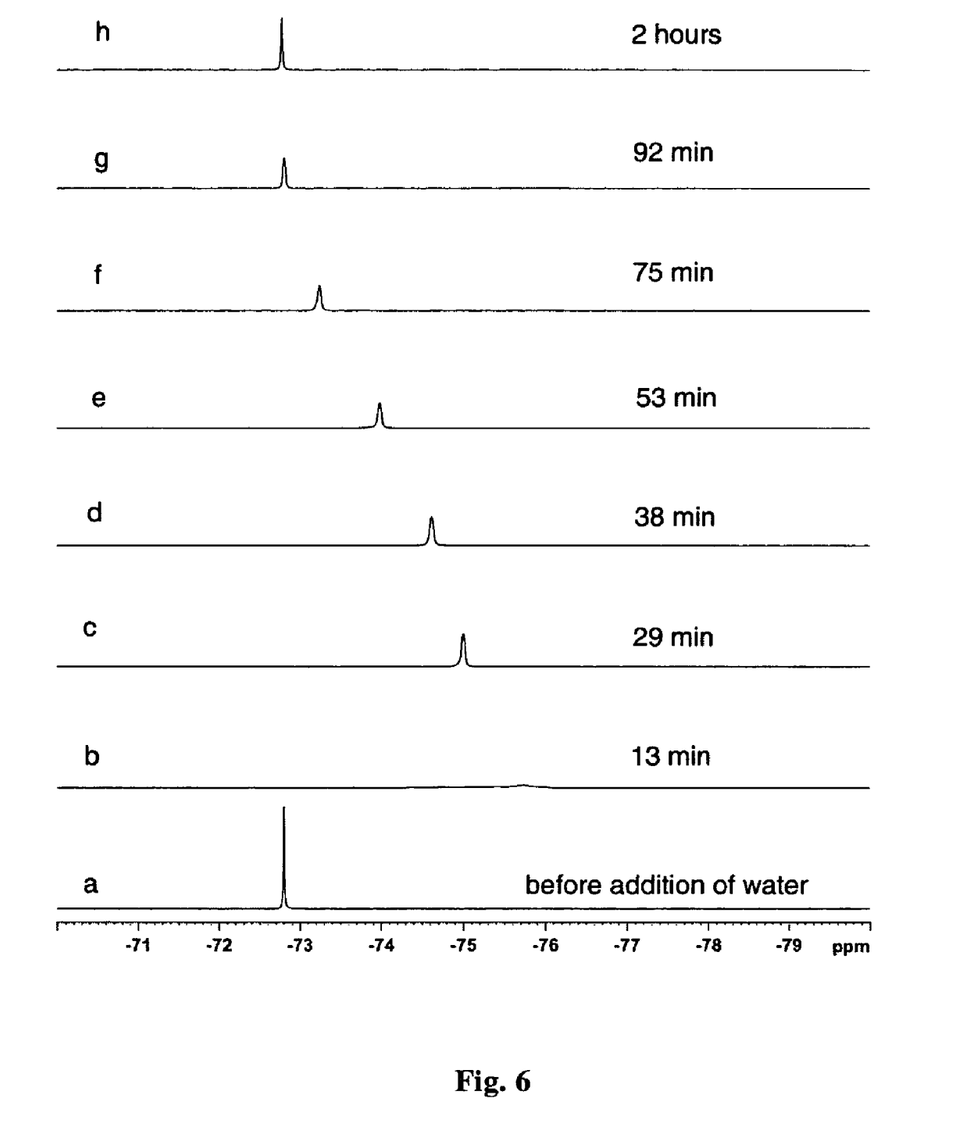

Detail of FIG. 5—FIG. 6: $^{19}$F NMR spectra (expanded area from Figure S-5) of the reaction of in-situ generated TBAF with 0.083 eq water in DMSO-d6. a, before addition of water; b~h, after addition of water.

Figure 7:
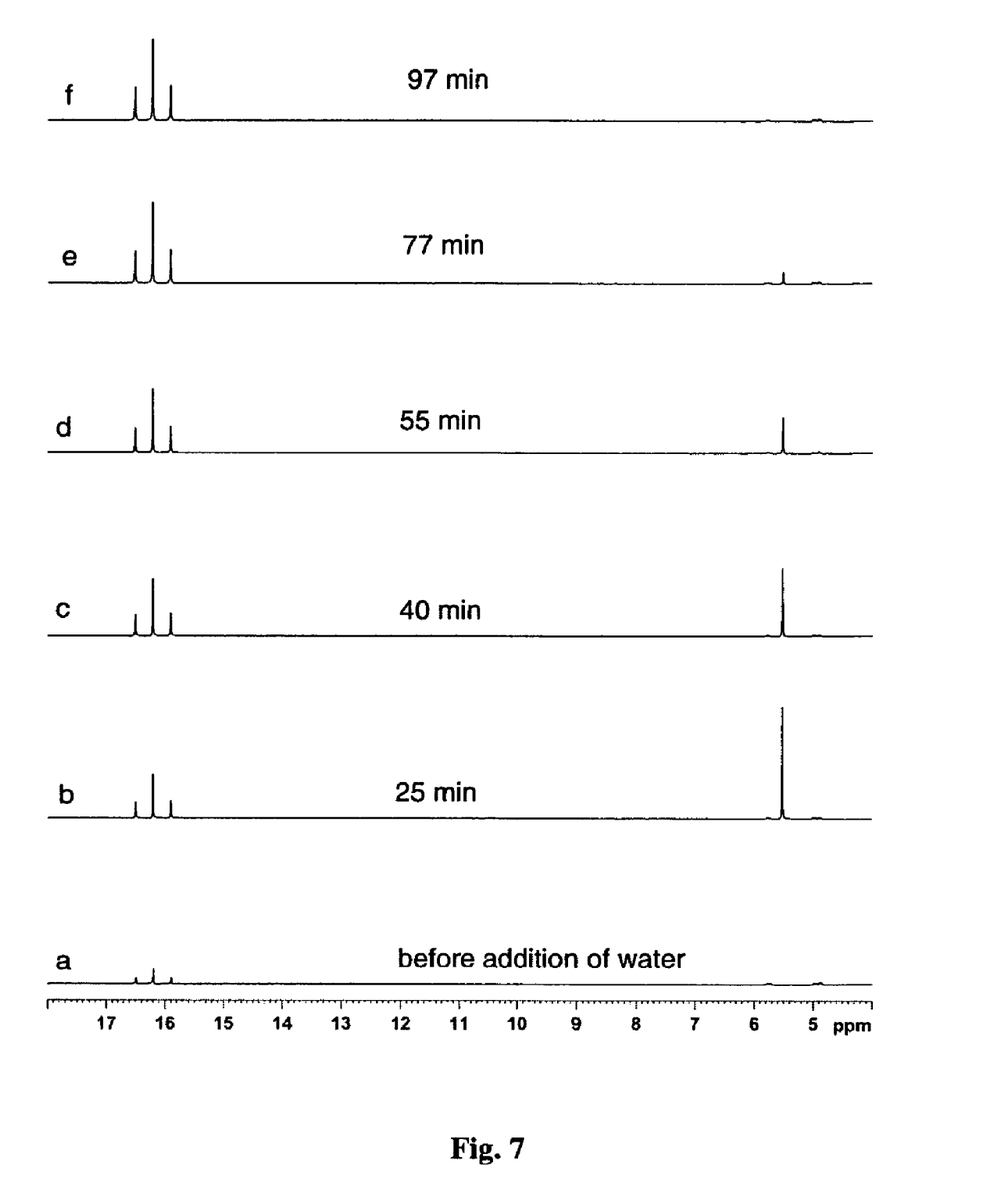

Reaction of in-situ generated TBAF with water—FIG. 7: $^1$H NMR spectra of the reaction of in-situ generated TBAF with 0.083 eq water in $(CD_3)_2SO$. a, before addition of water; b~f, after addition of water. The signal at 5.6 ppm is assigned to $H_2O$.

Figure 8:
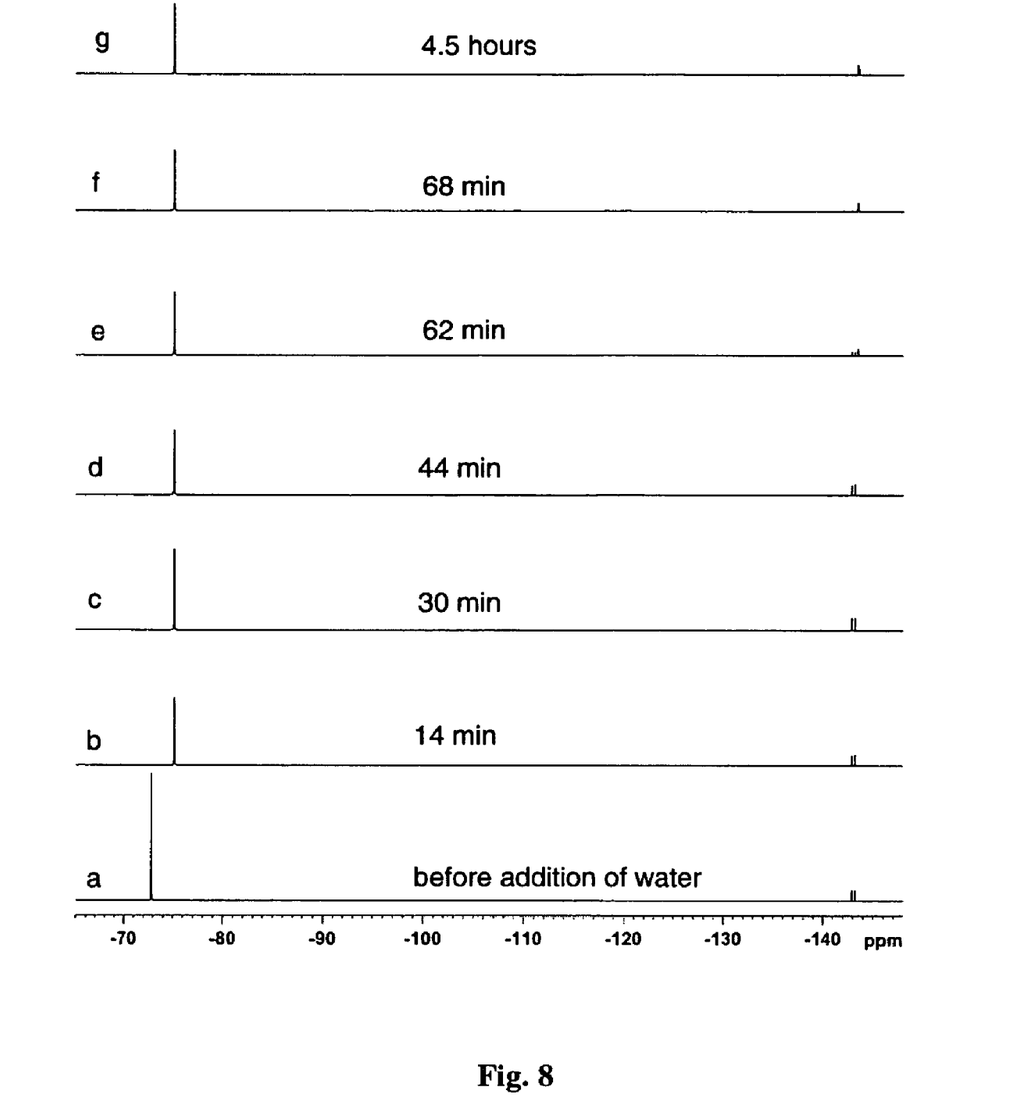

Reaction of isolated TBAF with water—FIG. 8: $^{19}$F NMR spectra of the reaction of isolated TBAF with 0.083 eq water in $(CD_3)_2SO$. a, before addition of water; b~g, after addition of water.

Figure 9:
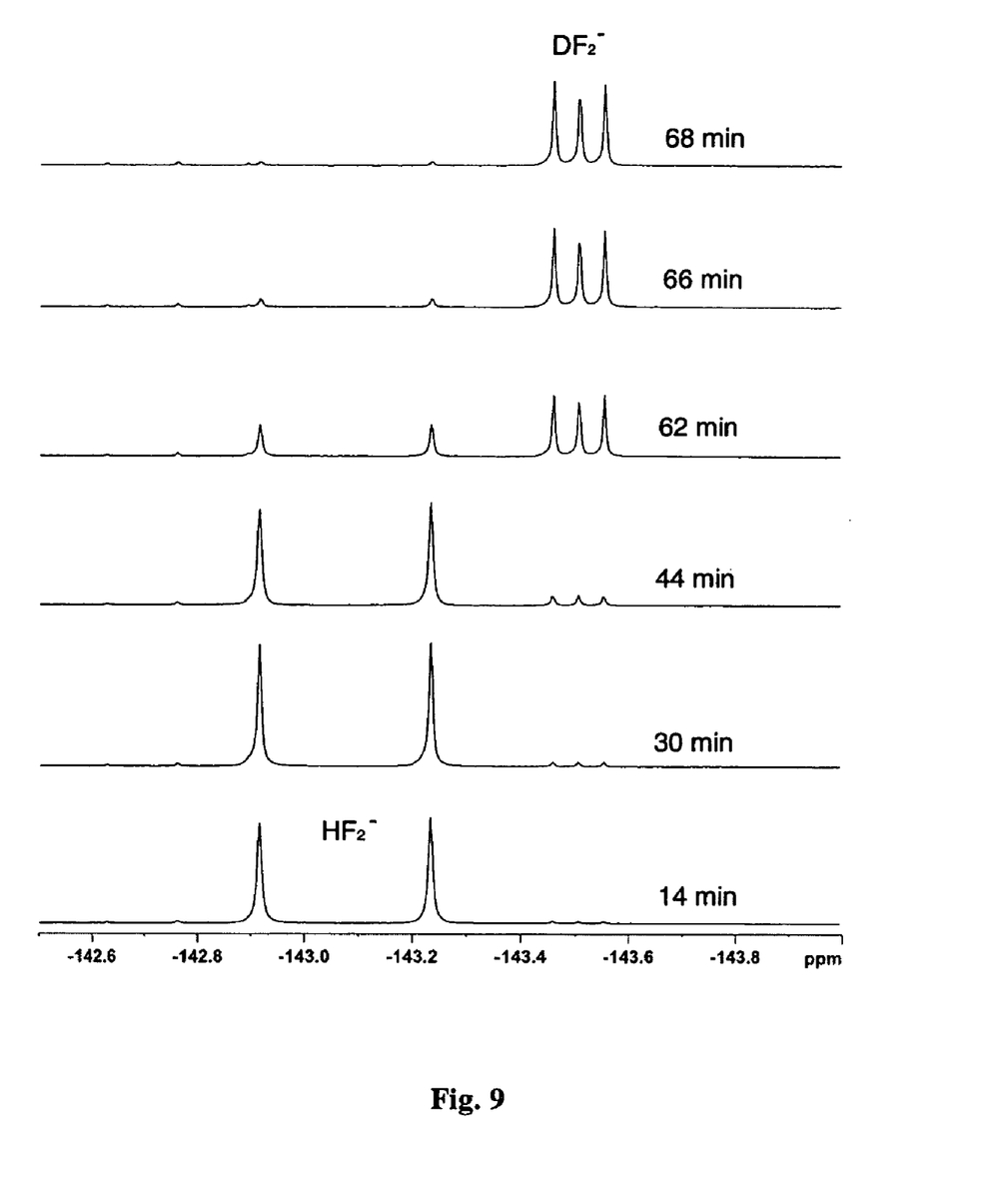

Detail of FIG. 8—FIG. 9: $^{19}$F NMR spectra of the reaction of isolated TBAF with 0.083 eq water in $(CD_3)_2SO$. (Detail from Figure S-8.)

Figure 10:
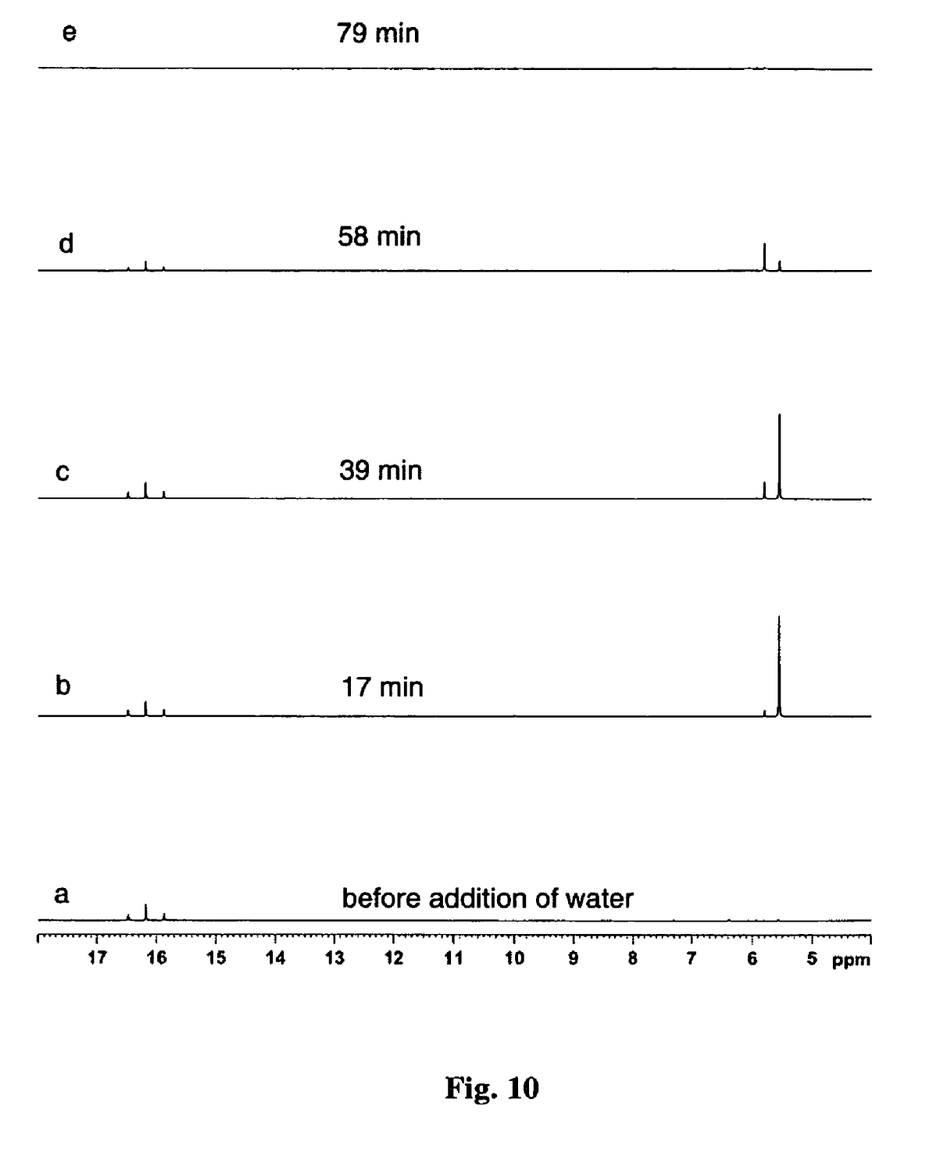

Reaction of isolated TBAF with water—FIG. 10: $^{19}$F NMR spectra of the reaction of isolated TBAF with 0.083 eq water in $(CD_3)_2SO$. a, before addition of water; b~e, after addition of water. The signal at 5.6 ppm is assigned to $H_2O$; the signal at 5.8 ppm is assigned to HOD.

The invention claimed is:

1. A method of synthesizing an anhydrous fluoride salt having the formula $[Q_nM]^{x+}F_x^-$, the method comprising a nucleophilic substitution of a fluorinated aromatic or fluorinated unsaturated organic compound with a salt having the formula $[Q_nM]^{x+}A_x^-$ in an inert polar, aprotic solvent wherein:
   M is nitrogen or phosphorus;
   Q groups are independently selected from the group consisting of an alkyl, an alkenyl, an alkynyl, an aryl, a heteroaryl, and a polymer;
   n is an integer such that said $[Q_nM]$ carries at least one formal positive charge;
   x is an integer defining the number of formal positive charge(s), +, carried by said $[Q_nM]$;
   $A^-$ is an anionic nucleophile selected from the group consisting of cyanide, isothiocyanate, isocyanate, cyanate, thiocyanate, alkylthiolates, arylthiolates, or azide; and
   F represents fluorine or a radioisotope thereof wherein the anhydrous fluoride salt contains less then 0.01% water of hydration.

2. The method of claim 1 wherein the nucleophilic substitution is conducted at a low temperature.

3. The method of claim 1 conducted at a temperature that is at least −35° C. and no greater than room temperature.

4. The method of claim 1 wherein said inert polar, aprotic solvent is tetrahydrofuran, dimethyl sulfoxide, diethyl ether, dioxane, dimethoxyethane, methyl tert-butyl ether, acetonitrile, acetone, methylethylketone, tetrahydrofuran, dimethylformamide, dimethylacetamide, N-methylpyrolidinone, butyronitrile, toluene, pyridine, benzonitrile, diphenyl ether, diethyl carbonate, or hexamethyiphosphoric triarmde.

5. The method of claim 1 wherein said fluorinated aromatic compound is a fluorinated benzene and said a fluorinated unsaturated organic compound is a fluorinated alkene or a fluorinated alkyne.

6. The method of claim 1 wherein said $[Q_nM]^{x+}A_x^-$, is a tetraalkylammonium cyanide, a trialkylarylammonium cyanide, a dialkyldiarylammonium cyanide, an alkyltriarylammonium cyanide, or a tetraarylammonium cyanide.

7. The method of claim 6 wherein said tetraalkylammonium cyanide is tetrabutylammonium cyanide.

8. The method of claim 1 wherein said fluorinated aromatic compound is hexafluorobenzene, octafluoronaphthalene, octafluorotoluene, pentafluorobenzonitrile, pentafluoropyridine or decafluorobiphenyl.

9. A method for preparation of an anhydrous tetraalkylammonium fluoride salt, the method comprising reacting a fluorinated aromatic compound, in a nucleophilic aromatic substitution reaction, with a tetraalkylammonium cyanide in an inert polar, aprotic solvent, to produce the anhydrous tetraalkylammonium fluoride salt, that contains less than 0.01% water of hydration.

10. The method of claim 9 wherein said tetraalkyl ammonium fluoride salt is tetrabutylammonium fluoride.

11. The method of claim 9 wherein said tetraalkylammonium cyanide is tetrabutylammonium cyanide.

12. The method of claim 9 wherein said fluorinated aromatic compound is hexafluorobenzene.

13. A method for preparation of a fluorinated compound, the method comprising reacting an anhydrous organic fluoride salt, in a nucleophilic substitution reaction, with an alkyl halide, a tosylate, a triflate, a nitroaromatic, a chloroaromatic, or an aromatic triflate compound to produce a fluorinated compound that contains less than 0.01% water of hydration.

14. A method for deprotection of a silylated species, comprising reacting the silylated species with an anhydrous organic fluoride salt that contains less than 0.01% water of hydration to deprotect the silylated species.

15. A method as set forth in claim 14 wherein the silylated species is a silylated aromatic, a silylated heteroaromatic, a silylated alcohol, or a silylated amine.

16. The method of claim 1 wherein $[Q_nM]^+$ is chiral.

* * * * *